Dec. 20, 1949. S. L. DAVENPORT Plant Pat. 906
APPLE TREE
Filed March 30, 1948
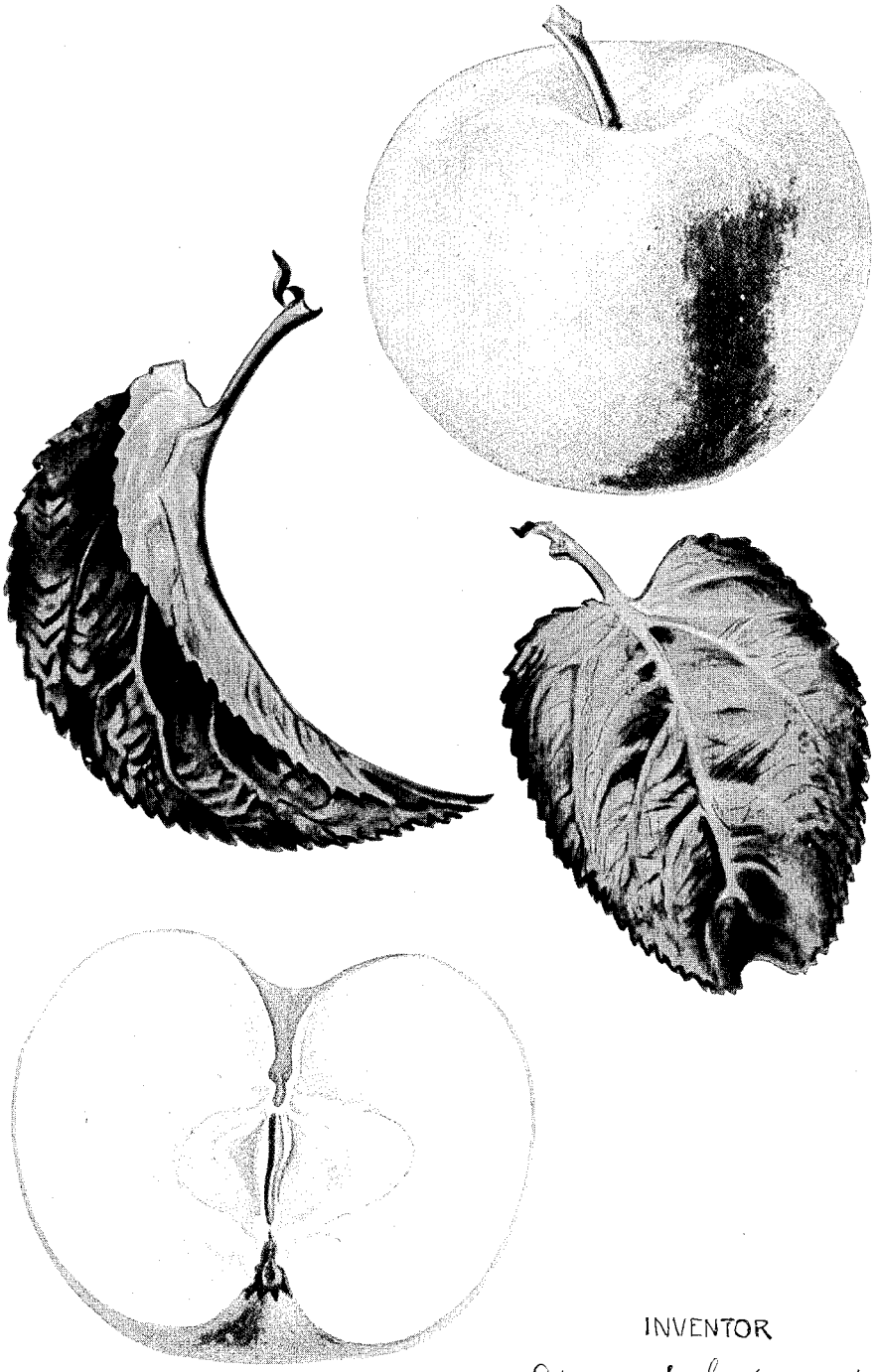
INVENTOR
Stearnes Lothrop Davenport
By Orville M. Kile
PLANT PATENT AGENT Patented Dec. 20, 1949

Plant Pat. 906

UNITED STATES PATENT OFFICE

906

APPLE TREE

Stearnes Lothrop Davenport, North Grafton, Mass., assignor to Kelly Brothers Nurseries, Inc., Dansville, N. Y.

Application March 30, 1948, Serial No. 17,988

1 Claim. (Cl. 47—62)

My present invention relates to a new and distinct variety of apple tree of the general McIntosh type. It originated as one of a number of seedlings planted by me from seed of McIntosh apples and grown in my orchards. When these seedlings began to bear, this particular one showed merit and I started propagation of it by grafting, at my orchards in Massachusetts. It has been tested at various places in the Northeast during the past ten years, with the same good results.

The new variety is intermediate between McIntosh and Wealthy but differs from both varieties, particularly in leaves and fruit. The leaves are usually folded and reflexed, have irregular rather distinct and moderately sharp serrations and rough dull surface. The fruit has high color, large size, uniform shape, firm flesh, and hangs well on the tree.

The accompanying illustrations show a side view and cross section view of a typical specimen of the fruit of the new variety; also leaf.

Following is a detailed description of the tree and fruit of my new variety, color names being in accordance with the usual dictionary meaning of the term.

*The tree*

Growth: Vigorous, upright spreading, rather open.

Hardiness: Hardy to winter cold where tested.

Bearing habits: Comes into bearing at an early age and tends strongly to bear annually.

Disease resistance: Much more resistant to scab, rusts, and other diseases common to apples than is the McIntosh.

Blooming season: Approximately the same as McIntosh.

Shoots: Rather stout, reddish brown, with a medium number of rather small lenticles, often elongated, not raised.

Leaves:

*Petiole.*—Short.

*Blade size.*—Medium.

*Form.*—Folded, reflexed, nearly even, ovate, spreading.

*Color.*—Medium to dark green.

*Texture.*—Rather thick.

*Serrations.*—Moderately sharp, medium size, irregular, rather distinct.

*Surface.*—Dull, rough, moderately pubescent.

*The fruit*

Maturity season: Matures with Baldwin.

Stem: Medium length, slender, clings well to tree.

Size: Uniform; large (2½ to 3 inches in length and 3 to 3¾ inches in transverse diameter).

Shape: Oblate to roundish. Uniform.

Color: Obscurely striped and splashed, with numerous conspicuous dots. These dots are peculiar to the variety and are medium sized, russet colored, and slightly raised. The basic color is 80 to 100 percent covered with dark red, which in turn is covered with a light pink bloom.

Skin texture: Thin; tough.

Flesh:

*Color.*—White.

*Texture.*—Melting to firm. Resembles Wealthy but is firmer and slightly coarser.

*Flavor.*—Moderately acid. Pleasant. Unlike any other apple.

*Quality.*—Good to very good.

Cavity: Deep, wide, flaring, oval, often russeted.

Basin: Moderately deep, abrupt, slightly ribbed.

Calyx: Usually open; tube short, wide, conic.

Stamens: Basal. Pollen abundant.

Core: Axile, oblate, medium in size and position.

Cells: Closed, rather large.

Carpels: Oval, obtuse, sometimes tufted.

Seeds: Plump, brown, medium sized. 5 to 7 in number.

Keeping qualities: Stands handling exceptionally well, keeps longer in storage than its parent McIntosh, but may shrivel in low humidity.

*Comparison*

The tree of my new variety is intermediate in features between McIntosh and Wealthy, although the leaves differ from either variety, as well as from any other variety known to me. In some respects the fruit also is intermediate between these two varieties, but it matures later and keeps much better than McIntosh. The texture resembles that of Wealthy but is firmer and a little coarser. The flavor also somewhat resembles that of Wealthy but is in fact unlike any other apple flavor.

In season and use this new variety may be compared to Baldwin. However my variety comes into bearing earlier and bears more regularly. The fruit of my variety is equal or superior to Baldwin in attractiveness, quality, and flavor and also it stands handling better and keeps longer.

Having thus disclosed my invention, I claim:

The new and distinct variety of apple tree, substantially as herein disclosed, characterized particularly by its habit of regular and early bearing; its disease resistance; its unusual leaves as described; and its late-maturing fruit which hangs well on the tree and has the following combination of outstanding qualities—distinctive moderately acid flavor, firm flesh, large size, uniform shape, high color with conspicuous dots, and good storage and handling qualities.

STEARNES LOTHROP DAVENPORT.

No references cited.